(12) United States Patent
Kobayashi et al.

(10) Patent No.: US 10,676,617 B2
(45) Date of Patent: *Jun. 9, 2020

(54) METHOD FOR PRODUCING ORGANOPOLYSILOXANE EMULSION COMPOSITION, AND EMULSION COMPOSITION

(71) Applicant: SHIN-ETSU CHEMICAL CO., LTD., Tokyo (JP)

(72) Inventors: Akihiro Kobayashi, Annaka (JP); Yuji Ando, Annaka (JP); Yuko Takada, Annaka (JP); Shunji Aoki, Annaka (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 198 days.

This patent is subject to a terminal disclaimer.

(21) Appl. No.: 15/309,000

(22) PCT Filed: May 12, 2015

(86) PCT No.: PCT/JP2015/063560
§ 371 (c)(1),
(2) Date: Nov. 4, 2016

(87) PCT Pub. No.: WO2015/174389
PCT Pub. Date: Nov. 19, 2015

(65) Prior Publication Data
US 2017/0073517 A1  Mar. 16, 2017

(30) Foreign Application Priority Data

May 14, 2014  (JP) ................................. 2014-100436

(51) Int. Cl.
*C08L 83/04* (2006.01)
*C08G 77/04* (2006.01)
*C08L 83/06* (2006.01)

(52) U.S. Cl.
CPC .............. *C08L 83/04* (2013.01); *C08G 77/04* (2013.01); *C08L 83/06* (2013.01)

(58) Field of Classification Search
CPC ................................. C08L 83/04; C08L 83/06
USPC ........................................................ 524/588
See application file for complete search history.

(56) References Cited

U.S. PATENT DOCUMENTS

| | | | | |
|---|---|---|---|---|
| 5,109,093 A | * | 4/1992 | Rees | ........................ C08G 77/08 528/14 |
| 6,207,781 B1 | * | 3/2001 | Halloran | ................... C07F 7/21 528/14 |
| 8,575,266 B2 | | 11/2013 | Brehm et al. | |
| 2003/0139481 A1 | | 7/2003 | Osawa | |
| 2004/0138373 A1 | * | 7/2004 | Hamachi | .................. A61K 8/06 524/588 |
| 2005/0142087 A1 | * | 6/2005 | Liu | ........................... A61K 8/06 424/66 |
| 2011/0269892 A1 | * | 11/2011 | Brehm | ................... C08G 77/06 524/500 |
| 2012/0171147 A1 | * | 7/2012 | Rautschek | ............... A61K 8/06 424/70.12 |
| 2014/0378553 A1 | | 12/2014 | Ando | |
| 2015/0174049 A1 | * | 6/2015 | Rautschek | ............... A61K 8/55 424/70.12 |

FOREIGN PATENT DOCUMENTS

| | | |
|---|---|---|
| JP | 34-2041 | 4/1959 |
| JP | 41-13995 | 8/1966 |
| JP | 2000-203216 * | 7/2000 |
| JP | 2003-212998 A | 7/2003 |
| JP | 2003-252994 A | 9/2003 |
| JP | 2006-291122 A | 10/2006 |
| JP | 4557147 B2 | 10/2010 |
| JP | 2011-236421 A | 11/2011 |
| WO | WO 2013/153833 A1 | 10/2013 |
| WO | 2012/119916 * | 2/2014 |
| WO | WO 2014/026900 A1 | 2/2014 |

OTHER PUBLICATIONS

English language translation JP 2000-203216 (Year: 2000).*
Extended European Search Report dated Dec. 21, 2017, in European Patent Application No. 15792271.7.
International Search Report, issued in PCT/JP2015/063560, dated Jun. 30, 2015.
Written Opinion of the International Searching Authority, issued in PCT/JP2015/063560, dated Jun. 30, 2015.

* cited by examiner

*Primary Examiner* — Margaret G Moore
(74) *Attorney, Agent, or Firm* — Birch, Stewart, Kolasch & Birch, LLP

(57) ABSTRACT

Provided is a method for producing an organopolysiloxane emulsion composition which contains an organopolysiloxane having a trialkyl group at a terminal thereof and having a viscosity of 50,000 mm$^2$/s or more at 25° C., within a shorter time compared with the conventional methods. A method for producing an emulsion composition which contains an organopolysiloxane having a viscosity of 50,000 mm$^2$/s or more at 25° C. and capped with a trialkylsilyl group, said method comprising: (I) emulsifying a mixture comprising (A) an organopolysiloxane, (B) a nonionic surfactant, (C) an anionic surfactant, (D-1) an acidic compound and (E-1) water to prepare an emulsion composition; (II) adding (D-2) an acidic compound and (E-2) water to the emulsion composition to perform emulsion polymerization; and (III) adding 0.001 part by mass or more of (F) a compound to the resultant product to perform emulsion polymerization again.

8 Claims, No Drawings

METHOD FOR PRODUCING ORGANOPOLYSILOXANE EMULSION COMPOSITION, AND EMULSION COMPOSITION

TECHNICAL FIELD

The present invention relates to a method for producing organopolysiloxane emulsion compositions which are useful in various fields, including cosmetics, household care compositions, and mold release agents. The invention relates also to such emulsion compositions.

BACKGROUND ART

In a variety of fields such as cosmetics, household care compositions and mold release agents, there is a desire for high-viscosity organopolysiloxanes to be rendered into fine emulsions. However, when high-viscosity organopolysiloxanes are directly emulsified, the size of the emulsion particles has a lower limit on the order of several microns; obtaining emulsions finer than this has been difficult. Accordingly, various methods for producing emulsions by emulsion polymerization have been investigated in order to obtain fine emulsion particles.

For example, methods for carrying out emulsion polymerization on a cyclic siloxane oligomer in an emulsified state by using a strong acid or a strong base are known (see, for example, Patent Documents 1 and 2). Using such methods, it is possible to obtain an emulsion having an emulsion particle size of 300 nm or less.

Of related interest, methods for the production of, by emulsion polymerization, stable emulsions containing high-viscosity organopolysiloxanes capped with trialkylsilyl groups have been investigated. For example, a method for producing a high-viscosity organopolysiloxane capped with trialkylsilyl groups in the presence of a hydroxy-terminated organopolysiloxane, a cyclic organopolysiloxane and a trialkyl-terminated organopolysiloxane having a viscosity at 25° C. of 50 mm$^2$/s or less has been investigated (Patent Document 3). In addition, a method of production in the presence of a hydroxy-terminated organopolysiloxane and a trialkyl-terminated organopolysiloxane having a viscosity at 25° C. of at least 55 mm$^2$/s has been investigated (Patent Document 4). However, under the above conditions, because trialkylsilyl end groups are present at the initial stage of polymerization, chain transfer and chain termination arise in parallel, and so the rate of polymerization is slower than in a system containing only a hydroxy-terminated organopolysiloxane. As a result, because setting the organopolysiloxane included in the emulsion to the desired viscosity takes time, one drawback is that octamethylcyclotetrasiloxane tends to be produced within the organopolysiloxane included in the resulting emulsion.

Therefore, setting the trialkyl-terminated organopolysiloxane within an emulsion to a desired viscosity in as short an emulsion polymerization time as possible is strongly desired not only for greater production efficiency, but also to suppress the octamethylcyclotetrasiloxane included in the organopolysiloxane within the emulsion.

PRIOR ART DOCUMENTS

Patent Documents

Patent Document 1: JP-B S34-2041
Patent Document 2: JP-B S41-13995
Patent Document 3: JP No. 4557147
Patent Document 4: JP-A 2011-236421

SUMMARY OF THE INVENTION

Problems to be Solved by the Invention

It is therefore an object of this invention to provide a method for producing an organopolysiloxane emulsion composition that can set the viscosity at 25° C. of a trialkyl-terminated organopolysiloxane included within the emulsion to at least 50,000 mm$^2$/s in a shorter time than in the prior art, wherein the organopolysiloxane included in the resulting emulsion preferably contains not more than 3,000 ppm of octamethylcyclotetrasiloxane. A further object of the invention is to provide an emulsion composition obtained by such a method.

Means for Solving the Problems

As a result of extensive investigations, the inventors have discovered that by: (1) at the initial stage of emulsion polymerization, polymerizing only an organopolysiloxane having silanol groups at the ends of the molecular chain, and (2) continuing to polymerize until the viscosity of the organopolysiloxane at 25° C. becomes 50,000 mm$^2$/s or more and then adding an end-capping compound and re-polymerizing, the organopolysiloxane included in the emulsion can be set to a viscosity of at least 50,000 mm$^2$/s and, moreover, the amount of octamethylcyclotetrasiloxane included in the resulting organopolysiloxane can be suppressed. Here and below, the viscosity in this invention refers to values measured at 25° C. with an Ostwald viscometer.

Accordingly, this invention provides the following method for producing an organopolysiloxane emulsion composition, and the following emulsion composition.

[1] A method for preparing an emulsion composition containing an organopolysiloxane that is capped with a trialkylsilyl group and has a viscosity at 25° C. of at least 50,000 mm$^2$/s, the method comprising the steps of, in order: (I) preparing an emulsion composition by emulsifying a mixture containing:
(A) 100 parts by weight of an organopolysiloxane of general formula (1) below having an octamethylcyclotetrasiloxane content of not more than 1,000 ppm $$HO(R^1{}_2SiO)_nH \qquad (1)$$

(wherein each $R^1$ is independently a hydrogen atom or a substituted or unsubstituted hydrocarbon group of 1 to 20 carbon atoms, and n is a number such that the organopolysiloxane has a viscosity at 25° C. of from 25 to 20,000 mm$^2$/s),
(B) 0 to 100 parts by weight of a nonionic surfactant,
(C) 0 to 100 parts by weight of an anionic surfactant,
(D-1) 0 to 100 parts by weight of an acidic compound (with the proviso that the combined amount of (B), (C) and (D-1) is at least 0.1 part by weight), and
(E-1) 1 to 10,000 parts by weight of water;
(II) adding to the resulting emulsion composition:
(D-2) 0 to 25 parts by weight of an acidic compound (with the proviso that the combined amount of (D-1) and (D-2) is at least 0.1 part by weight), and
(E-2) 0 to 10,000 parts by weight of water, and subsequently carrying out emulsion polymerization at a temperature below 40° C. until the viscosity at 25° C. of the organopolysiloxane becomes at least 50,000 mm$^2$/s; and (III) adding at least 0.001 part by weight of:
(F) a compound of general formula (2) or (3) below $$R^2_3SiOH \quad (2)$$

$$R^2_3SiO(R^3_2SiO)_m SiR^2_3 \quad (3)$$

(wherein each $R^2$ is independently an alkyl group of 1 to 18 carbon atoms which may be interrupted by an oxygen atom, each $R^3$ is independently a hydrogen atom or a substituted or unsubstituted hydrocarbon group of 1 to 20 carbon atoms, and m is a number such that the viscosity at 25° C. of the organopolysiloxane is from 0.65 to 100 mm$^2$/s) and again carrying out emulsion polymerization.

[2] An emulsion composition obtained by the preparation method of [1] above, comprising an organopolysiloxane that is capped with a trialkylsilyl group and has a viscosity at 25° C. of at least 50,000 mm$^2$/s.

Advantageous Effects of the Invention

This invention enables an emulsion composition containing an organopolysiloxane that is capped with a trialkylsilyl group and has a viscosity at 25° C. of at least 50,000 mm$^2$/s to be obtained in a short time. In addition, an emulsion composition of excellent stability can be obtained.

EMBODIMENT FOR CARRYING OUT THE INVENTION

The materials used in the production method of the invention are described below.

<(A) Organopolysiloxane>

Component (A) is an organopolysiloxane of general formula (1) below which has an octamethylcyclotetrasiloxane content of not more than 1,000 ppm.

$$HO(R^1_2SiO)_nH \quad (1)$$

(wherein each $R^1$ is independently a hydrogen atom or a substituted or unsubstituted hydrocarbon group of 1 to 20 carbon atoms, and n is a number such that the organopolysiloxane has a viscosity at 25° C. of from 25 to 20,000 mm$^2$/s)

Each $R^1$ is independently a hydrogen atom or a substituted or unsubstituted hydrogen carbon group of 1 to 20 carbon atoms. Unsubstituted hydrocarbon groups of 1 to 20 carbon atoms are exemplified by alkyl groups of 1 to 20 carbon atoms, cycloalkyl groups of 3 to 20 carbon atoms, alkenyl groups of 2 to 20 carbon atoms, aryl groups o 6 to 20 carbon atoms, and aralkyl groups of 7 to 20 carbon atoms. Illustrative examples include alkyl groups such as methyl, ethyl, propyl, butyl, pentyl, hexyl, heptyl, octyl, nonyl, decyl, dodecyl, tetradecyl, hexadecyl and octadecyl groups; cycloalkyl groups such as cyclopentyl and cyclohexyl groups; alkenyl groups such as vinyl and allyl groups; and aryl groups such as phenyl, tolyl and naphthyl groups. Substituted hydrocarbon groups of 1 to 20 carbon atoms are exemplified by the aforementioned monovalent hydrocarbon groups of 1 to 20 carbon atoms in which some of the hydrogen atoms are substituted with halogen atoms, amino groups, acryloxy groups, methacryloxy groups, epoxy groups, mercapto groups, carboxyl groups or hydroxyl groups. Preferred examples include hydrocarbon groups of 1 to 6 carbon atoms, such as methyl, ethyl, propyl, butyl and phenyl groups. The organopolysiloxane of formula (1) is even more preferably one in which at least 80% of all the $R^1$ groups are methyl groups.

The subscript n is a number such that the organopolysiloxane has a viscosity at 25° C. of from 25 to 20,000 mm$^2$/s, more preferably from 40 to 10,000 mm$^2$/s, and even more preferably from 400 to 6,000 mm$^2$/s. At a viscosity below 25 mm$^2$/s, it may be necessary to lengthen the emulsion polymerization time in order to set the organopolysiloxane included in the target emulsion to the desired viscosity, and the amount of octamethylcyclotetrasiloxane that forms as a by-product during emulsion polymerization may increase. On the other hand, when the viscosity is too high, the stability of the target emulsion to be obtained may worsen.

The octamethylcyclotetrasiloxane content in the organopolysiloxane of component (A) is not more than 1,000 ppm (weight basis, the same applies below), and preferably not more than 500 ppm. The content of octamethylcyclotetrasiloxane has no particular lower limit, and may be 0 ppm.

<(B) Nonionic Surfactant>

The nonionic surfactant is exemplified by polyoxyalkylene alkyl ethers, polyoxyalkylene alkyl phenyl ethers, polyoxyalkylene alkyl esters, polyoxyalkylene sorbitan alkyl esters, polyethylene glycol, polypropylene glycol and diethylene glycol. One nonionic surfactant may be used alone, or two or more may be suitably selected and used together. Of these, a nonionic surfactant of general formula (4) is preferred.

$$R^4O(EO)_p(PO)_qH \quad (4)$$

wherein, $R^4$ is a linear or branched alkyl group of 8 to 30 carbon atoms, and preferably 8 to 20 carbon atoms, EO represents an ethylene oxide group and PO represents a propylene oxide group, these being arranged randomly or as blocks. The subscripts p and q are each independently integers from 0 to 100, and preferably from 0 to 50, with the proviso that p+q>0. In general formula (4), $R^4$ is preferably a linear or branched alkyl group of 8 to 13 carbon atoms, and p and q are preferably each independently from 0 to 25, such that 0<p+q≤50.

The amount of component (B) used may be set to from 0 to 100 parts by weight per 100 parts by weight of component (A). That is, the addition of component (B) is optional and not required. When component (B) is added, the amount of addition is in a range of up to not more than 100 parts by weight. The amount of such addition is preferably from 1 to 50 parts by weight, and more preferably from 3 to 20 parts by weight.

<(C) Anionic Surfactant>

The anionic surfactant serving as component (C) is exemplified by the following. One anionic surfactant may be used alone, or two or more may be suitably selected and used together.

(1) Alkyl Sulfates of General Formula (5)

$$R^5OSO_3M \quad (5)$$

wherein, $R^5$ is a linear or branched alkyl group of 6 to 30, and preferably 8 to 20, carbon atoms, M is an alkali metal ion such as potassium or sodium, an alkaline earth metal ion such as magnesium or calcium, or a tertiary ammonium ion such as ammonium or triethanolammonium.

In general formula (5), $R^5$ is a linear or branched alkyl group of 6 to 12 carbon atoms, and M, from the standpoint of the emulsification effect, is preferably a sodium, potassium, ammonium or triethanolammonium ion.

Illustrative examples of alkyl sulfates of general formula (5) include alkali metal salts (e.g., lithium, sodium, and potassium salts), alkaline earth metal salts (e.g., magnesium and calcium salts), and triethanolammonium and ammonium salts of hexyl sulfuric acid, octyl sulfuric acid, decyl sulfuric acid, dodecyl sulfuric acid, tetradecyl sulfuric acid, hexadecyl sulfuric acid, octadecyl sulfuric acid and eicosyl sulfuric acid.

(2) Alkylbenzene Sulfonates of General Formula (6)

$$R^5-C_6H_4-SO_3M \qquad (6)$$

wherein, $R^5$, as defined in general formula (5), is a linear or branched alkyl group of 6 to 30 carbon atoms. M, as defined in general formula (5), is an alkali metal ion such as potassium or sodium, an alkaline earth metal ion such as magnesium or calcium, or a tertiary ammonium ion such as ammonium or triethanolammonium.

In general formula (6), $R^5$ is a linear or branched alkyl group of 6 to 12 carbon atoms, and M, from the standpoint of the emulsification effect, is preferably a sodium, potassium, ammonium or triethanolammonium ion.

Illustrative examples of alkylbenzene sulfonates of general formula (6) include salts of hexylbenzene sulfonic acid, octylbenzene sulfonic acid, decylbenzene sulfonic acid, dodecylbenzene sulfonic acid, tetradecylbenzene sulfonic acid and hexadecylbenzene sulfonic acid.

(3) Higher Fatty Acid Salts

Illustrative examples of higher fatty acid salts include alkali metal salts (e.g., lithium salts, sodium salts, potassium salts), alkaline earth metal salts (e.g., magnesium salts, calcium salts), and triethanolammonium salts and ammonium salts of, for example, lauric acid, stearic acid, oleic acid and linolenic acid.

(4) Polyoxyethylene Alkyl Ether Sulfates of General Formula (7)

$$R^5O(EO)_i(PO)_jSO_3M \qquad (7)$$

Here, $R^5$, as defined in general formula (5), is a linear or branched alkyl group of 6 to 30 carbon atoms. M, as defined in general formula (5), is an alkali metal ion such as potassium or sodium, an alkaline earth metal ion such as magnesium or calcium, or a tertiary ammonium ion such as ammonium or triethanolammonium. EO is an ethylene oxide group and PO is a propylene oxide group, these being arranged randomly or as blocks. The subscripts i and j are each independently an integer from 0 to 100, provided that i+j>0.

Illustrative examples of polyoxyethylene alkyl ether sulfates include alkali metal salts (e.g., lithium salts, sodium salts, potassium salts), alkaline earth metal salts (e.g., magnesium salts, calcium salts), and triethanolammonium salts and ammonium salts of polyoxyethylene hexyl ether sulfuric acid, polyoxyethylene octyl ether sulfuric acid, polyoxyethylene decyl ether sulfuric acid, polyoxyethylene dodecyl ether sulfuric acid, polyoxyethylene tetradecyl ether sulfuric acid, polyoxyethylene hexadecyl ether sulfuric acid, polyoxyethylene octadecyl ether sulfuric acid and polyoxyethylene eicosyl ether sulfuric acid.

(5) Polyoxyethylene Alkyl Phenyl Ether Sulfate Salts of General Formula (8)

$$R^5-C_6H_4-O(EO)_i(PO)_jSO_3M \qquad (8)$$

wherein, $R^5$, as defined in general formula (5), is a linear or branched alkyl group of 6 to 30 carbon atoms. M, as defined in general formula (5), is an alkali metal ion such as potassium or sodium, an alkaline earth metal ion such as magnesium or calcium, or a tertiary ammonium ion such as ammonium or triethanolammonium. EO, PO, i and j are as defined in general formula (7). That is, EO is an ethylene oxide group and PO is a propylene oxide group, these being arranged randomly or as blocks. The subscripts i and j are each independently an integer from 0 to 100, provided that i+j>0.

Illustrative examples of polyoxyethylene alkyl phenyl ether sulfate salts include alkali metal salts (e.g., lithium salts, sodium salts, potassium salts), alkaline earth metal salts (e.g., magnesium salts, calcium salts), and triethanolammonium salts and ammonium salts of polyoxyethylene hexyl phenyl ether sulfuric acid, polyoxyethylene octyl phenyl ether sulfuric acid, polyoxyethylene decyl phenyl ether sulfuric acid, polyoxyethylene dodecyl phenyl ether sulfuric acid, polyoxyethylene tetradecyl phenyl ether sulfuric acid and polyoxyethylene hexadecyl phenyl ether sulfuric acid.

Component (C) may be used in an amount of from 0 to 100 parts by weight per 100 parts by weight of component (A). The addition of component (C) is optional and not required. When component (C) is added, the amount of addition is in a range of not more than 100 parts by weight, preferably from 0 to 25 parts by weight, and more preferably from 0 to 15 parts by weight.

The combined amount of components (B), (C) and (D-1) per 100 parts by weight of component (A) is at least 0.1 part by weight. There is no particular upper limit, although the combined amount of these components is typically not more than about 300 parts by weight, and preferably from 0.1 to 100 parts by weight.

<(D) Acidic Compound>

The acidic compounds used as component (D) are component (D-1) used in Step (I) and component (D-2) used in Step (II). Components (D-1) and (D-2) are respectively of a single type used alone or of two or more types used in suitable combinations.

Examples of component (D) are given below. (1) Alkyl sulfuric acids of general formula (9), and alkylbenzene sulfonic acids of general formula (10).

$$R^6OSO_3H \qquad (9)$$

wherein, $R^6$ is a linear or branched alkyl group of 6 to 30 carbon atoms.

$$R^6-C_6H_4-SO_3H \qquad (10)$$

wherein, $R^6$, as defined in general formula (9), is a linear or branched alkyl group of 6 to 30 carbon atoms.

In general formulas (9) and (10), $R^6$ is preferably a linear or branched alkyl group of 6 to 12 carbon atoms.

Illustrative examples of alkyl sulfuric acids of general formula (9) include hexyl sulfuric acid, octyl sulfuric acid, decyl sulfuric acid, dodecyl sulfuric acid, tetradecyl sulfuric acid, hexadecyl sulfuric acid, octadecyl sulfuric acid and eicosyl sulfuric acid.

Illustrative examples of alkylbenzene sulfonic acids of general formula (10) include hexylbenzene sulfonic acid, octylbenzene sulfonic acid, decylbenzene sulfonic acid, dodecylbenzene sulfonic acid, tetradecylbenzene sulfonic acid and hexadecylbenzene sulfonic acid.

(2) Higher Fatty Acids

Illustrative examples include lauric acid, stearic acid, oleic acid and linolenic acid.

(3) Polyoxyethylene Alkyl Ether Sulfuric Acids of General Formula (11)

$$R^6O(EO)_s(PO)_tSO_3H \qquad (11)$$

wherein, $R^6$, as defined in general formula (9), is a linear or branched alkyl group of 6 to 30 carbon atoms. EO is an ethylene oxide group and PO is a propylene oxide group, these being arranged randomly or as blocks. The subscripts s and t are each independently an integer from 0 to 100, provided that s+t>0.

Illustrative examples include polyoxyethylene hexyl ether sulfuric acid, polyoxyethylene octyl ether sulfuric acid, polyoxyethylene decyl ether sulfuric acid, polyoxyethylene dodecyl ether sulfuric acid, polyoxyethylene tetradecyl ether sulfuric acid, polyoxyethylene hexadecyl ether sulfuric acid, polyoxyethylene octadecyl ether sulfuric acid and polyoxyethylene eicosyl ether sulfuric acid.

(4) Polyoxyethylene Alkyl Phenyl Ether Sulfuric Acids of General Formula (12)

$$R^6-C_6H_4-O(EO)_s(PO)_tSO_3H \qquad (12)$$

wherein, $R^6$, as defined in general formula (9), is a linear or branched alkyl group of 6 to 30 carbon atoms. EO, PO, s and t are as defined in general formula (11). That is, EO is an ethylene oxide group and PO is a propylene oxide group, these being arranged randomly or as blocks. The subscripts s and t are each independently an integer from 0 to 100, provided that s+t>0.

Illustrative examples include polyoxyethylene hexyl phenyl ether sulfuric acid, polyoxyethylene octyl phenyl ether sulfuric acid, polyoxyethylene decyl phenyl ether sulfuric acid, polyoxyethylene dodecyl phenyl ether sulfuric acid, polyoxyethylene tetradecyl phenyl ether sulfuric acid and polyoxyethylene hexadecyl phenyl ether sulfuric acid.

(5) Brnsted Acids

Illustrative examples include hydrochloric acid, hydrobromic acid, sulfuric acid, chlorosulfonic acid, phosphoric acid, orthophosphoric acid, metaphosphoric acid, polyphosphoric acid, boric acid, nitric acid, benzenesulfonic acid, trifluoromethanesulfonic acid, carbonic acid, chloroacetic acid, trichloroacetic acid, acetic acid, acrylic acid, benzoic acid, trifluoroacetic acid, citric acid, crotonic acid, formic acid, fumaric acid, maleic acid, malonic acid, tannic acid, itaconic acid, lactic acid, tartaric acid, oxalic acid, phthalic acid, succinic acid, cation-exchange resins, acidic zeolites, acid-activated fuller's earth and acid-activated carbon black.

When component (D) is used in Step (I), because component (D) acts as a catalyst, component (D) need not be used in Step (II). Steps (I) and (II) are shown below.

The amount of component (D) used, i.e., the combined amount of components (D-1) and (D-2), is at least 0.1 part by weight, preferably at least 0.3 part by weight, and more preferably at least 0.5 part by weight, per 100 parts by weight of component (A). At less than 0.1 part by weight, the polymerization rate becomes very slow. The amount of component (D) used, although not subject to any particular upper limit, is typically not more than 125 parts by weight.

In Step (I), the amount of component (D-1) used per 100 parts by weight of component (A) is typically from 0 to 100 parts by weight, preferably from 0 to 30 parts by weight, and more preferably from 0 to 15 parts by weight. When component (D-1) is added in Step (I), the amount of addition is preferably from 0.1 to 30 parts by weight.

Although component (D-2) may or may not be added in Step (II), the amount of component (D-2) added per 100 parts by weight of component (A) is preferably from 0 to 25 parts by weight, more preferably from 0 to 20 parts by weight, and even more preferably from 0 to 10 parts by weight. When component (D-2) is added in Step (II), the amount is preferably from 0.1 to 30 parts by weight.

<(E) Water>

The water used as component (E) is component (E-1) used in Step (I) and component (E-2) used in Step (II). The amount of component (E-1) used in Step (I) is from 1 to 10,000 parts by weight per 100 parts by weight of component (A), and differs according to the type of emulsifying apparatus (emulsifier) used when reducing the size of the emulsion particles.

When using an emulsifier such as a high-pressure homogenizer or colloid mill (an apparatus that emulsifies by feeding the respective ingredients into a gap between a disk that rotates at a high speed and a stationary disk) that uses pressure to reduce the size of emulsion particles, the amount of component (E-1) used per 100 parts by weight of component (A) is preferably from 1 to 10,000 parts by weight, more preferably from 4 to 6,000 parts by weight, and even more preferably from 6 to 4,000 parts by weight.

For example, when employing an emulsifier such as a homogenizing disperser or a homogenizing mixer that uses shear forces to reduce the size of the emulsion particles, the amount of component (E-1) used per 100 parts by weight of component (A) is preferably from 1 to 10 parts by weight, more preferably from 2 to 8 parts by weight, and even more preferably from 4 to 6 parts by weight. When more than 10 parts by weight is added here, it may be difficult to obtain an emulsion composition containing fine emulsion particles having a particle size of 300 nm or less. On the other hand, when less than 1 part by weight is added, it may be difficult to obtain an oil-in-water emulsion.

In Step (II), component (E-2) may or may not be added, the amount of component (E-2) added per 100 parts by weight of component (A) being preferably not more than 10,000 parts by weight, and more preferably from 0 to 10,000 parts by weight. When component (E-2) is added, the amount of component (E-2) is preferably from 0.1 to 1,000 parts by weight.

<(F) Organosilicon Compound>

Component (F) is an organosilicon compound of general formula (2) or (3). One such compound may be used alone or two or more may be suitably selected and used together.

$$R^2_3SiOH \qquad (2)$$

$$R^2_3SiO(R^3_2SiO)_mSiR^2_3 \qquad (3)$$

wherein, each $R^2$ is independently an alkyl group of 1 to 18 carbon atoms that may be interrupted with an oxygen atom, each $R^3$ is independently a hydrogen atom or a substituted or unsubstituted hydrocarbon group of 1 to 20 carbon atoms, and m is a number such that the organopolysiloxane has a viscosity at 25° C. of from 0.65 to 100 mm²/s.

In general formulas (2) and (3), $R^2$ is an alkyl group of 1 to 18 carbon atoms, $R^3$ is an unsubstituted hydrocarbon group of 1 to 20 carbon atoms, such as an alkyl group of 1 to 20 carbon atoms, a cycloalkyl group of 3 to 20 carbon atoms, an alkenyl group of 2 to 20 carbon atoms, an aryl group of 6 to 20 carbon atoms or an aralkyl group of 7 to 20 carbon atoms. Illustrative examples include alkyl groups such as methyl, ethyl, propyl, butyl, pentyl, hexyl, heptyl, octyl, nonyl, decyl, dodecyl, tetradecyl, hexadecyl and octadecyl groups; cycloalkyl groups such as cyclopentyl and cyclohexyl groups; alkenyl groups such as vinyl and allyl groups; and aryl groups such as phenyl, tolyl and naphthyl groups. Examples of substituted hydrocarbon groups of 1 to 20 carbon atoms include the above-mentioned monovalent hydrocarbon groups of 1 to 20 carbon atoms in which some of the hydrogen atoms are substituted with halogen atoms, amino groups, acryloxy groups, methacryloxy groups, epoxy groups, mercapto groups, carboxyl groups or hydroxyl groups. A hydrocarbon group of 1 to 6 carbon atoms is preferred, examples of which include methyl, ethyl, propyl, butyl and phenyl groups. It is even more preferable for at least 80% of all $R^1$ groups to be methyl groups.

In general formula (3), m is a number such that the organosiloxane of general formula (3) has a viscosity at 25° C. of from 0.65 to 100 mm²/s, preferably from 0.65 to 50 mm²/s, and even more preferably from 0.65 to 20 mm²/s.

Component (F) is exemplified by trimethylsilanol, triethylsilanol, tripropylsilanol, hexamethyldisiloxane, hexaethyldisiloxane, hexapropyldisiloxane and polydimethylsiloxane.

The amount of component (F) is suitably selected according to the polysiloxane degree of polymerization and end-group capping ratio following polymerization. The amount is at least 0.001 part by weight per 100 parts by weight of component (A). Although not subject to any particular upper limit, the amount of component (F) is generally not more than 100 parts by weight.

The inventive method of production is described below.

<Step (I)>

An emulsion composition is prepared by emulsifying a mixture containing component (A), one or more of any of components (B), (C) and (D-1), and component (E-1). Specifically, an emulsion composition is obtained by emulsifying components (A), (B), (C), (D-1) and (E-1), components (A), (B), (C) and (5-1), components (A), (B), (D-1) and (E-1), components (A), (C), (D-1) and (E-1), components (A), (C) and (E-1), or components (A), (D-1) and (E-1). Here, emulsification can be carried out using an emulsifier such as a homogenizing disperser, a homogenizing mixer, a colloid mill, a line mixer, a universal mixer, an ultra mixer, a planetary mixer, a combination mixer or a high-pressure homogenizer.

In this step, the emulsification temperature is preferably from 1 to 80° C. When component (D-1) is added, a cyclization reaction also proceeds at the same time, and so emulsification is preferably carried out at a temperature of below 40° C. Should emulsification be carried out at a temperature of 40° C. or more, the production of octamethylcyclotetrasiloxane may increase. Accordingly, the temperature is preferably less than 30° C., and more preferably less than 25° C.

In Step (I), the mixture is mixed under the application of high shear forces until the size of the emulsion particles in the emulsion composition becomes preferably 300 nm or less, more preferably 200 nm or less, and even more preferably 150 nm or less. The smaller the size of the emulsion particles obtained in Step (I), the higher the increase in the rate of polymerization in Step (II), thus shortening the polymerization time. Because the size of the emulsion particles in the emulsion composition obtained in Step (I) is 300 nm or less, the ultimate size of the emulsion particles obtained in the next step is 300 nm or less.

<Step (II)>

After optionally adding (D-2) an acidic compound and (E-2) water to the resulting emulsion composition, emulsion polymerization is carried out at a temperature of under 40° C. until the viscosity at 25° C. of the organopolysiloxane becomes at least 50,000 mm²/s.

In cases where component (E-2) has thus been added to the emulsion composition, emulsification/dispersion may be additionally carried out thereafter with an emulsifier such as a high-pressure homogenizer.

Next, the emulsion composition is emulsion polymerized. The polymerization step is carried out at a temperature of below 40° C. for up to 48 hours. When polymerization is carried out at a temperature of 40° C. or above, the production of octamethylcyclotetrasiloxane may increase. Hence, the polymerization temperature is preferably below 25° C., and more preferably below 15° C. When the polymerization time exceeds 48 hours, the production of octamethylcyclotetrasiloxane may increase. Hence, the polymerization time is preferably from 1 to 40 hours, and more preferably from 5 to 30 hours.

The organopolysiloxane produced by emulsion polymerization in step (II) has a viscosity at 25° C. of at least 50,000 mm²/s, preferably at least 75,000 mm²/s, and more preferably at least 100,000 mm²/s. Although the viscosity is not subject to any particular upper limit, it is generally not more than 20,000,000 mm²/s.

<Step (III)>

Following emulsion polymerization, component (F) is added and emulsion polymerization is again carried out (re-polymerization). The emulsion polymerization time following component (F) addition is preferably from 0.01 to 15 hours, more preferably from 0.05 to 10 hours, and even more preferably from 0.1 to 5 hours. From the standpoint of suppressing the amount of octamethylcyclotetrasiloxane production due to emulsion polymerization as the cyclization reaction proceeds and suppressing the content of octamethylcyclotetrasiloxane in the organopolysiloxane, the re-polymerization time is preferably not more than 15 hours.

<Other Treatment>

Once polymerization has ended, the resulting emulsion composition is generally neutralized with a basic substance. Examples of the basic substance include sodium hydroxide, potassium hydroxide, sodium bicarbonate, and amine compounds such as triethanolamine and triethylamine.

The silicone concentration can be adjusted at this time by adding water. Also, additives such as preservatives and fungicides may be added in order to increase the shelf stability of the emulsion composition.

For weatherstripping, textile treatment and resin modification applications, by adding an alkoxysilane such as $R^7{}_3Si(OR^8)$, $R^7{}_2Si(OR^8)_2$ or $R^7Si(OR^8)_3$ in step (I) in which emulsification is carried out, step (II) in which emulsion polymerization is carried out, or to the emulsion composition after carrying out neutralization, branched units and various types of functional groups can be introduced onto the resulting organopolysiloxane chain. Here, $R^7$ is a hydrogen atom or a substituted or unsubstituted hydrocarbon group of 1 to 20, and preferably 1 to 6, carbon atoms, illustrative examples of which include methyl, ethyl, propyl, butyl and phenyl groups. $R^8$ is the same or a different alkyl group of 1 to 20 carbon atoms or is a hydrogen atom.

The inventive emulsion composition containing an organopolysiloxane that is capped with trialkylsilyl groups and has a viscosity at 25° C. of at least 50,000 mm²/s in the production method of the invention is described below.

The viscosity of the organopolysiloxane capped with trialkylsilyl groups within the emulsion composition is at least 50,000 mm²/s, preferably at least 75,000 mm²/s, and more preferably at least 100,000 mm²/s. Although not subject to any particular upper limit, the viscosity is generally not more than about 10,000,000 mm²/s. The method of measurement is explained under "Viscosity of Organopolysiloxane" in the subsequently described examples.

The average size of the emulsion particles in the emulsion composition is preferably not more than 300 nm, and more preferably not more than 200 nm. Although not subject to any particular lower limit, the average particle size is generally at least about 30 nm. In this invention, a very fine emulsion composition in which the average size of the emulsion particles is not more than 300 nm can be obtained. The average size of the emulsion particles is the median diameter obtained by a laser diffraction/scattering method.

The content of octamethylcyclotetrasiloxane included in the organopolysiloxane capped with trialkylsilyl groups is preferably not more than 3,000 ppm, more preferably not more than 2,000 ppm, and even more preferably not more than 1,000 ppm. Although not subject to any particular lower limit, the content is 0 ppm or more. The method of measurement is explained under "Octamethylcyclotetrasiloxane Content in Organopolysiloxane" in the subsequently described Examples.

The content of decamethylcyclopentasiloxane included in the organopolysiloxane capped with trialkylsilyl groups is preferably not more than 3,000 ppm, more preferably not more than 2,000 ppm, and even more preferably not more than 1,000 ppm. Although not subject to any no particular lower limit, the content is 0 ppm or more.

EXAMPLES

The invention is illustrated more fully below by way of Examples and Comparative Examples, although these Examples are not intended to limit the invention. All references to "parts" are by weight. Viscosities are values measured at 25° C. with an Ostwald viscometer.

Example 1

Ten parts of (B) polyoxyethylene tridecyl ether (10 moles EO), 4 parts of (C) triethanolamine dodecylbenzene sulfonate and 8 parts of (E-1) water were added to 100 parts of (A) an organopolysiloxane having silanol groups on the ends of the molecular chain (octamethylcyclotetrasiloxane content, ≤50 ppm) and a viscosity of 5,000 mm$^2$/s, after which emulsification was carried out with a homogenizing disperser. Next, 125.2 parts of (E-2) water was added to the resulting emulsion and dilution/dispersion was carried out with a homogenizing mixer, following which 4 parts of (D-2) dodecylbenzene sulfonic acid was added and emulsion polymerization was carried out at 15° C. for 10 hours (the viscosity of the organopolysiloxane at 25° C. was at least 50,000 mm$^2$/s). Next, 0.21 part of (F) hexamethyldisiloxane was added to the resulting emulsion and emulsion polymerization was again carried out for 1 hour, following which 2.4 parts of triethanolamine was added to the resulting emulsion and dilution/dispersion was carried out with a homogenizing mixer, thereby giving an emulsion composition. The results are shown in Table 1.

Example 2

Ten parts of (B) polyoxyethylene tridecyl ether (10 moles EO), 4 parts of (D-1) dodecylbenzene sulfonic acid, and 8 parts of (E-1) water were added to 100 parts of (A) an organopolysiloxane having silanol groups on the ends of the molecular chain (octamethylcyclotetrasiloxane content, ≤50 ppm) and a viscosity of 5,000 mm$^2$/s, after which emulsification was carried out with a colloid mill. The resulting emulsion was emulsion polymerized at 15° C. for 10 hours (the viscosity of the organopolysiloxane at 25° C. was at least 50,000 mm$^2$/s). Next, 0.21 part of (F) hexamethyldisiloxane was added to the resulting emulsion and emulsion polymerization was again carried out for 1 hour, following which 2.4 parts of triethanolamine and 125.2 parts of water were added to the resulting emulsion and dilution/dispersion was carried out with a homogenizing mixer, giving an emulsion composition. The results are shown in Table 1.

Example 3

Six parts of (B) polyoxyalkylene (10 moles EO, 10 moles PO) branched decyl ether, 8 parts of (D-1) dodecylbenzene sulfonic acid, and 6 parts of (E-1) water were added to 100 parts of (A) an organopolysiloxane having silanol groups on the ends of the molecular chain (octamethylcyclotetrasiloxane content, ppm) and a viscosity of 5,000 mm$^2$/s, and the mixture was emulsified with a homogenizing disperser. The resulting emulsion was emulsion polymerized at 0° C. for 15 hours (the viscosity of the organopolysiloxane at 25° C. was at least 50,000 mm$^2$/s). Next, 0.063 part of (F) trimethylsilanol was added to the resulting emulsion and emulsion polymerization was again carried out for 1 hour, following which 4.8 parts of triethanolamine and 125.2 parts of water were added to the resulting emulsion and dilution/dispersion was carried out with a homogenizing mixer, thereby giving the target emulsion composition. The results are shown in Table 1.

Comparative Example 1

Ten parts of (B) polyoxyethylene tridecyl ether (10 moles EO), 4 parts of (C) triethanolamine dodecylbenzene sulfonate and 8 parts of (E-1) water were added to a mixed oil of 100 parts of (A) an organopolysiloxane having silanol groups on the ends of the molecular chain (octamethylcyclotetrasiloxane content, ppm) and a viscosity of 5,000 mm$^2$/s and 0.21 part of (F) hexamethyldisiloxane, and the mixture was emulsified with a homogenizing disperser. Next, 125.2 parts of (E-2) water was added and dilution/dispersion was carried out with a homogenizing mixer, following which 4 parts of (D-2) dodecylbenzene sulfonic acid was added and the resulting emulsion was separately emulsion polymerized for 11 hours and for 22 hours at 15° C. Triethanolamine, 2.4 parts, was added to the resulting emulsions, and each of the emulsions was subjected to dilution/dispersion with a homogenizing mixer, thereby giving the target emulsion compositions. The results are shown in Table 1.

As is apparent from the results in Table 1, because hexamethyldisiloxane was added during preparation of the emulsions in this Comparative Example, the viscosity of the base oil only rose to 70,000 mm$^2$/s when emulsion polymerization was carried out for 10 hours, and to 140,000 mm$^2$/s when emulsion polymerization was carried out for 20 hours.

Comparative Example 2

Six parts of (B) polyoxyalkylene (10 moles EO, 10 moles PO) branched decyl ether, 8 parts of (D-1) dodecylbenzene sulfonic acid and 6 parts of (E-1) water were added to a mixed oil of 100 parts of (A) an organopolysiloxane having silanol groups on the ends of the molecular chain (octamethylcyclotetrasiloxane content, ppm) and a viscosity of 5,000 mm$^2$/s and 0.063 part of (F) trimethylsilanol, and the mixture was emulsified with a homogenizing disperser. The resulting emulsion was separately emulsion polymerized for 16 hours and for 32 hours at 0° C. Triethanolamine, 4.8 parts, and 125.2 parts of water were added to the resulting emulsions, and each of the emulsion was subjected to dilution/dispersion with a homogenizing mixer, thereby giving the target emulsion compositions. The results are shown in Table 1.

The properties indicated below for the emulsion compositions obtained in the above Examples were measured or evaluated by the methods shown below.

[Average Particle Size of Emulsion]

This was the median diameter measured with a model LA-920 laser diffraction/scattering type particle size analyzer (Horiba, Ltd.).

[Viscosity of Organopolysiloxane]

Isopropyl alcohol, 300 g, was added under stirring to 300 g of the prepared emulsion composition. Only the organopolysiloxane that separated out was collected and dried at 105° C. for 3 hours, following which the viscosity at 25° C. was measured with a rotational viscometer at 25° C.

[Octamethylcyclotetrasiloxane Content in Organopolysiloxane]

The emulsion composition, 0.1 g, was extracted (3 hours of shaking) with 10 mL of acetone containing 20 ppm (weight basis) of tetradecane as an internal standard, then left to stand overnight, following which the acetone layer was collected and the octamethylcyclotetrasiloxane was quantitatively determined by gas chromatographic analysis. The amount of organopolysiloxane is based on the amount of organopolysiloxane used.

[Stability of Emulsion]

The emulsion composition, 100 g, was placed in a 100 mL glass jar and left to stand for one month at 50° C., following which the appearance was examined. When the emulsion formed a single uniform phase and no separation was observed, the stability was rated as "Good." When even a little separation into two phases was observed, the stability was rated as "NG."

TABLE 1

|  |  | Polymerization temperature (° C.) | Polymerization time (hr) | Re-polymerization time (hr) | Average particle size (nm) | Viscosity (mm²/s) | $D_4$ content (ppm) | Stability (50° C., 1 month) |
|---|---|---|---|---|---|---|---|---|
| Example | 1 | 15 | 10 | 1 | 120 | 180,000 | 550 | good |
|  | 2 | 15 | 10 | 1 | 100 | 220,000 | 500 | good |
|  | 3 | 0 | 15 | 1 | 140 | 1,500,000 | 1,050 | good |
| Comparative | 1 | 15 | 11 | 0 | 120 | 70,000 | 560 | NG |
| Example |  | 15 | 22 | 0 | 120 | 140,000 | 1,100 | NG |
|  | 2 | 0 | 16 | 0 | 140 | 750,000 | 1,200 | NG |
|  |  | 0 | 32 | 0 | 140 | 1,300,000 | 3,100 | NG |

Note:
$D_4$: Octamethylcyclotetrasiloxane

INDUSTRIAL APPLICABILITY

The inventive composition has an excellent stability and is very pleasant to use, making it particularly useful for cosmetics and household goods. For example, it can be used in hair care products such as shampoos and rinses.

It can also be used as a protective material for furniture and sundry articles, as a mold release agent for molds used when manufacturing rubber products and plastic products, and as a textile treatment for imparting water repellency and softness to fibers.

The invention claimed is:

1. A method for preparing an emulsion composition containing an organopolysiloxane that is capped with a trialkylsilyl group and has a viscosity at 25° C. of at least 100,000 mm²/s, the method comprising the steps of, in order:
   (I) preparing an emulsion composition by emulsifying a mixture containing:
       (A) 100 parts by weight of an organopolysiloxane of general formula (1) below having an octamethylcyclotetrasiloxane content of not more than 1,000 ppm $$HO(R^1{}_2SiO)_nH \tag{1}$$

wherein each $R^1$ is independently a hydrogen atom or a substituted or unsubstituted hydrocarbon group of 1 to 20 carbon atoms, and n is a number such that the organopolysiloxane has a viscosity at 25° C. of from 25 to 20,000 mm²/s,
       (B) 1 to 100 parts by weight of a nonionic surfactant,
       (C) 0 to 100 parts by weight of an anionic surfactant,
       (D-1) 0 to 100 parts by weight of an acidic compound (with the proviso that the combined amount of (B), (C) and (D-1) is at least 0.1 part by weight), and
       (E-1) 1 to 10,000 parts by weight of water;
   (II) adding to the resulting emulsion composition:
       (D-2) 0 to 25 parts by weight of an acidic compound (with the proviso that the combined amount of (D-1) and (D-2) is at least 0.1 part by weight), and
       (E-2) 0 to 10,000 parts by weight of water,
   and subsequently carrying out emulsion polymerization at a temperature below 40° C. until the viscosity at 25° C. of the organopolysiloxane becomes at least 100,000 mm²/s,
   (III) adding at least 0.001 part by weight of:
       (F) a compound of general formula (2) or (3) below $$R^2{}_3SiOH \tag{2}$$

$$R^2{}_3SiO(R^3{}_2SiO)_mSiR^2{}_3 \tag{3}$$

wherein each $R^2$ is independently an alkyl group of 1 to 18 carbon atoms which may be interrupted by an oxygen atom, each $R^3$ is independently a hydrogen atom or a substituted or unsubstituted hydrocarbon group of 1 to 20 carbon atoms, and m is a number such that the viscosity at 25° C. of the organopolysiloxane of general formula (3) is from 0.65 to 100 mm²/s, and again carrying out emulsion polymerization, and the emulsion polymerization time from addition of the component (F) is from 0.01 to 15 hours, and
   (IV) neutralizing the resulting emulsion composition after emulsion polymerization with a basic substance, wherein the acidic compound ((D-1) and (D-2)) is selected from the group consisting of
       (1) alkyl sulfuric acids of general formula (9), and alkylbenzene sulfonic acids of general formula (10), $$R^6OSO_3H \tag{9}$$

wherein, $R^6$ is a linear or branched alkyl group of 6 to 30 carbon atoms, $$R^6-C_6H_4-SO_3H \tag{10}$$

wherein, $R^6$ is a linear or branched alkyl group of 6 to 30 carbon atoms,
       (2) higher fatty acids,
       (3) polyoxyethylene alkyl ether sulfuric acids of general formula (11), $$R^6O(EO)_s(PO)_tSO_3H \quad (11)$$

wherein, $R^6$ is a linear or branched alkyl group of 6 to 30 carbon atoms, EO is an ethylene oxide group and PO is a propylene oxide group, these being arranged randomly or as blocks, and the subscripts s and t are each independently an integer from 0 to 100, provided that s+t>0, and (4) polyoxyethylene alkyl phenyl ether sulfuric acids of general formula (12)

$$R^6—C_6H_4—O(EO)(PO)_tSO_3H \quad (12)$$

wherein, $R^6$ is a linear or branched alkyl group of 6 to 30 carbon atoms, EO is an ethylene oxide group and PO is a propylene oxide group, these being arranged randomly or as blocks, and the subscripts s and t are each independently an integer from 0 to 100, provided that s+t>0.

2. The emulsion composition preparation method of claim 1, wherein m in compound (F) of general formula (3) used in step (III) is a number such that the viscosity at 25° C. of the organopolysiloxane is from 0.65 to 20 mm²/s.

3. The emulsion composition preparation method of claim 1 or 2, wherein emulsion particles in the emulsion composition have an average particle size of not more than 300 nm.

4. The emulsion composition preparation method of claim 1, wherein the trialkylsilyl-capped organopolysiloxane in the emulsion composition has a viscosity at 25° C. of not more than 10,000,000 mm²/s.

5. The emulsion composition preparation method of claim 1, wherein the content of octamethylcyclotetrasiloxane included in the trialkylsilyl-capped organopolysiloxane within the emulsion composition is not more than 3,000 ppm.

6. The emulsion composition preparation method of claim 1, wherein the organopolysiloxane produced by emulsion polymerization in step (II) has a viscosity at 25° C. of not more than 20,000,000 mm²/s.

7. The emulsion composition preparation method of claim 1, wherein $R^1$ in formula (1) is methyl, ethyl, propyl, butyl, or phenyl.

8. The emulsion composition preparation method of claim 1, wherein component (F) is trimethylsilanol, triethylsilanol, tripropylsilanol, hexamethyldisiloxane, hexaethyldisiloxane, hexapropyldisiloxane, or polydimethylsiloxane.

* * * * *